United States Patent
Gibson et al.

(10) Patent No.: US 9,291,511 B2
(45) Date of Patent: Mar. 22, 2016

(54) SHOCK OR IMPACT SENSOR

(71) Applicant: XEROX CORPORATION, Norwalk, CT (US)

(72) Inventors: George A. Gibson, Fairport, NY (US); Linn C. Hoover, Webster, NY (US)

(73) Assignee: XEROX CORPORATION, Norwalk, CT (US)

( * ) Notice: Subject to any disclaimer, the term of this patent is extended or adjusted under 35 U.S.C. 154(b) by 278 days.

(21) Appl. No.: 14/034,112

(22) Filed: Sep. 23, 2013

(65) Prior Publication Data

US 2015/0082861 A1    Mar. 26, 2015

(51) Int. Cl.
| | |
|---|---|
| *G01L 1/00* | (2006.01) |
| *G01L 1/04* | (2006.01) |
| *G01P 15/06* | (2006.01) |
| *G01P 15/18* | (2013.01) |
| *G01P 15/03* | (2006.01) |

(52) U.S. Cl.
CPC . *G01L 1/00* (2013.01); *G01L 1/044* (2013.01); *G01L 1/04* (2013.01); *G01N 2203/0664* (2013.01); *G01P 15/036* (2013.01); *G01P 15/06* (2013.01); *G01P 15/18* (2013.01)

(58) Field of Classification Search
CPC ....... G01P 15/036; G01P 15/18; G01P 15/00; G01P 15/06
USPC .................. 73/12.01, 12.06, 12.09, 862.381, 73/862.53, 862.637
See application file for complete search history.

(56) References Cited

U.S. PATENT DOCUMENTS

| | | | | |
|---|---|---|---|---|
| 2,825,297 | A * | 3/1958 | Harrison | G01P 15/036 116/203 |
| 5,604,336 | A * | 2/1997 | Johnson | G01G 3/1412 177/229 |
| 6,080,944 | A * | 6/2000 | Itoigawa | H01H 1/0036 200/61.45 R |
| 7,409,851 | B2 * | 8/2008 | Ilic | G01N 29/022 422/82.01 |
| 7,886,573 | B2 * | 2/2011 | Zadesky | G01P 15/06 73/12.01 |
| 8,074,489 | B2 * | 12/2011 | Ishikawa | G01D 3/10 116/202 |
| 8,234,993 | B2 * | 8/2012 | Naruishi | G01L 5/008 116/200 |
| 8,240,270 | B2 * | 8/2012 | Naruishi | B65D 79/02 116/200 |
| 8,307,775 | B2 * | 11/2012 | Naruishi | G01C 9/10 116/200 |
| 8,677,802 | B2 * | 3/2014 | Hower | G01D 21/00 73/12.01 |
| 2002/0092359 | A1* | 7/2002 | Lange | B82Y 35/00 73/779 |
| 2009/0307827 | A1* | 12/2009 | Aspray | A42B 3/046 2/425 |
| 2010/0015808 | A1* | 1/2010 | Ozawa | G01N 3/30 438/703 |
| 2011/0051144 | A1* | 3/2011 | Wilfinger | G01C 19/721 356/459 |
| 2014/0224018 | A1* | 8/2014 | Whitesides | G01P 15/0802 73/514.33 |

* cited by examiner

*Primary Examiner* — Lisa Caputo
*Assistant Examiner* — Jonathan Dunlap
(74) *Attorney, Agent, or Firm* — MH2 Technology Law Group LLP (57) ABSTRACT

A sensor for detecting impact is generally provided. The sensor may include a deformable beam. The deformable beam may include a first end, a second end, and an elongated body extending therebetween. At least the second end is coupled to a support structure. Further, the deformable beam may be configured to bend from a first configuration to a deformed configuration when the sensor experiences an acceleration above a predetermined threshold.

19 Claims, 8 Drawing Sheets

SHOCK OR IMPACT SENSOR

TECHNICAL FIELD

The present disclosure relates generally to impact and/or shock sensors.

BACKGROUND

A variety of packaged goods may be sensitive to shock, impact forces, etc. Sensors that indicate such shock/impact are often secured to packages with fragile contents and may be highly visible so as to deter and detect rough treatment or mishandling of the packages. Such sensors are available in a variety of levels of sophistication, from single use, g-force sensors to electronic devices that can be reset and/or can store a time history of multiple impacts, etc.

The more-sophisticated devices may provide a higher degree of information; however, these devices often rely on a source of on-board power, e.g., a battery. As such, the devices may be effective for a limited amount of time, both on a per-cycle and a lifetime basis. Further, both the simple and sophisticated sensors may result in increased costs associated with the packaging. As such, many users may opt to avoid such additional costs.

SUMMARY

Embodiments of the disclosure may provide a sensor for detecting impact. The sensor may include a deformable beam. The deformable beam may include a first end, a second end, and an elongated body extending therebetween. At least the second end is coupled to a support structure. Further, the deformable beam may be configured to bend from a first configuration to a deformed configuration when the sensor experiences an acceleration above a predetermined threshold.

Embodiments of the disclosure may also provide a package including a plurality of faces. The package may also include a first sensor coupled with at least one of the plurality of faces. The first sensor may include a deformable beam including a first end, a second end, and an elongate body extending therebetween. At least the second end may be positionally fixed to a support structure. Further, the deformable beam may be configured to deflect from a first configuration to a deformed configuration when the first sensor experiences an acceleration above a predetermined threshold.

Embodiments of the disclosure may further provide an apparatus for detecting an impact event. The apparatus may include a housing comprising an endwall and a sidewall, with the endwall and the sidewall at least partially defining an interior of the housing. The apparatus may also include a deformable beam including a paper, a polymer, a coated paper, or a combination thereof. The deformable beam further includes first and second ends. The second end is coupled with the endwall of the housing and the first end is distal to the second end and is free to move in the interior of the housing, such that the deformable beam supported from the endwall as a cantilever, or the first end is coupled with a second endwall of the housing such that the deformable beam is simply supported in the housing. At least a portion of the deformable beam defines a visible wrinkle when and after the apparatus experiences an acceleration above a predetermined threshold.

It is to be understood that both the foregoing general description and the following detailed description are exemplary and explanatory only and are not restrictive of the present teachings, as claimed.

BRIEF DESCRIPTION OF THE DRAWINGS

The accompanying drawing, which is incorporated in and constitutes a part of this specification, illustrates an embodiment of the present teachings and together with the description, serves to explain the principles of the present teachings.

It should be noted that some details of the figure have been simplified and are drawn to facilitate understanding of the embodiments rather than to maintain strict structural accuracy, detail, and scale.

DETAILED DESCRIPTION

Reference will now be made in detail to embodiments of the present teachings, examples of which are illustrated in the accompanying drawing. In the drawings, like reference numerals have been used throughout to designate identical elements. In the following description, reference is made to the accompanying drawing that forms a part thereof, and in which is shown by way of illustration a specific exemplary embodiment in which the present teachings may be practiced. The following description is, therefore, merely exemplary.

Figure 1:
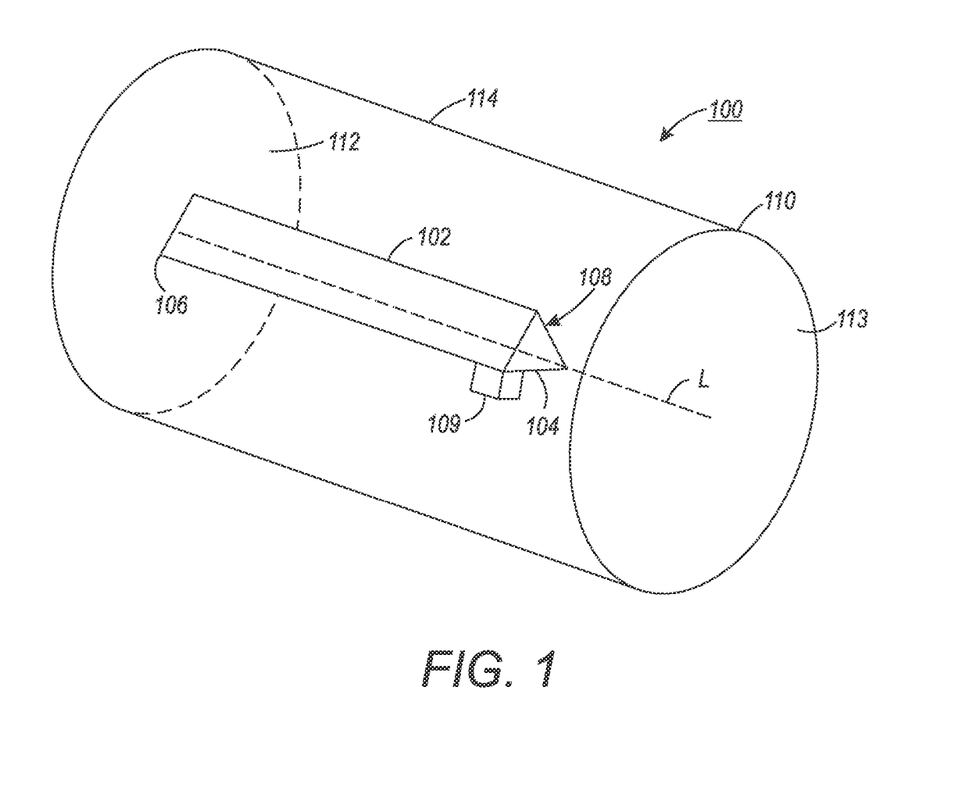
FIG. 1 illustrates a conceptual perspective view of a sensor, according to an embodiment.
Figure 2:
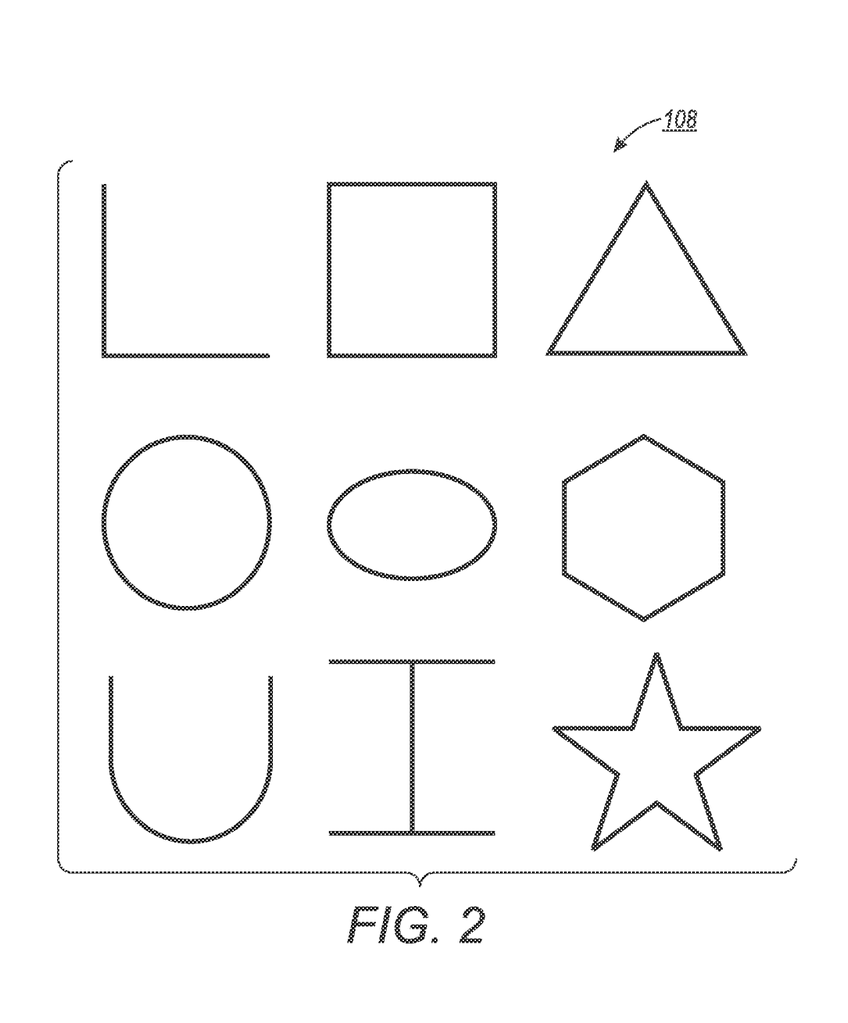
FIG. 2 illustrates a view of several cross-sections consistent with one or more embodiments of the sensor.

FIG. 1 illustrates a sensor 100 for detecting and indicating shock or impulse forces, according to an embodiment. The sensor 100 may include an elongated, deformable beam 102 extending between first and second ends 104, 106. The deformable beam 102 may define a cross-section 108, perpendicular to a longitudinal axis L the beam 102. The cross-section 108 may have, in some examples, a polygonal shape, such as a triangle (as shown), square, rectangle, star, regular or irregular polygon, etc. In other embodiments, the cross-section 108 may be L-shaped, I-shaped, rectangular, circular, elliptical, toroidal, or the like. FIG. 2 illustrates several non-limiting examples of such cross-sections 108. Further, the cross-section 108 may or may not be uniform along the beam 102. In some embodiments, the cross-section 108 may vary among two or more of shapes and/or may change in size as proceeding between the first and second ends 104, 106.

In some embodiments, the deformable beam 102 may be contained in a housing 110 that may serve as a support structure for the deformable beam 102. In other embodiments, the deformable beam 102 may not be in a housing but may, instead, be positioned in a cavity of a container, partially surrounded by flanges or a wall of such a container, or otherwise situated. In such an embodiment, the flanges, wall, etc. may provide the support structure. Accordingly, while the illustrated embodiments of the sensor 100 are illustrated as including the housing 110, it will be appreciated that sensors 100 that do not include a housing are expressly contemplated herein and may be employed without departing from the present disclosure.

The housing 110 may be, for example, tubular shaped, as shown, or may be any other shape. For example, the housing 110 may be constructed form a cardboard tube, and may include at least one endwall (two shown: 112 and 113) and at least one sidewall 114. In other embodiments, any other shape of housing 110, e.g., cube, prism, etc., may be employed, with any suitable number of endwalls and/or sidewalls.

In one example, the second end 106 of the deformable beam 102 may be secured to the housing 110, for example, the endwall 112. The second end 106 may be secured to the housing 110 using any suitable process and/or device, such as adhesive, plastic welding, integral forming, fastening, etc. The first end 104 may, in some embodiments, remain unattached to the housing 110, such that the deformable beam 102 is disposed in a cantilever configuration (i.e., "cantilevered") in the housing 110. Accordingly, in at least one embodiment, the first end 104 may be free to move with respect to the housing 110 (or any other structure to which the beam 102 is secured), while the second end 106 remains coupled with the endwall 112. In other embodiments, frangible or deformable supports, e.g., thin wires, filament, coiled springs, paper or polymer supports, or the like, may be employed to, at least temporarily, secure the first end 104 of the deformable beam 102 with respect to the housing 110 (or any other structure to which the beam 102 is secured).

In at least one embodiment, the deformable beam 102 may be made from a material that has minimal resiliency, such that the structural integrity of the deformable beam 102 is compromised when a sufficient bending moment is applied thereto, e.g., when the sensor 100 is accelerated beyond a certain threshold. As such, the deformable beam 102 may not resiliently spring back to its original configuration after a sufficient bending moment is applied. In some instances, this may be referred to as a "permanent deformation;" that is, without substantial reconstruction of the deformable beam 102, the deformable beam 102, once deformed, remains deformed, and may continue to evidence signs of previous deformation even if it is attempted to be deformed back into its original position, thereby providing an indication of a history of impact/shock forces.

In an embodiment, the material from which the deformable beam 102 is constructed may be a paper medium of any suitable construction, weight, thickness, etc., which may be folded or rolled so as to take the form of a suitable embodiment of the cross-section 108. In another embodiment, the material may be a polymer such as polyethylene terephthalate (PET), polypropylene such as a biaxially oriented polypropylene (BOPP), or any other suitable polymer. In some cases, a thin sheet of such polymer may be folded into shape, similar to paper. In other embodiments, the polymer may be molded or formed into shape and may act similarly to the paper embodiment. In yet another embodiment, the material from which the sensor 100 is at least partially constructed may be a combination of paper and polymer, such as a coated or varnished paper. The use of a coating or varnishing of the paper may prevent absorption of water from the environment, such as humidity in the air, that would otherwise be absorbed by the paper of the deformable beam 102 and alter its strength characteristics.

In various embodiments, the cross-section 108 shape, the material, the thickness of the material, length of the deformable beam 102 and/or the thickness of the cross-section 108 may be selected so as to resist bending up to a predetermined threshold of force. The threshold force may be set, for example, to that expected to be caused by acceleration due to an impact force, such as from dropping the sensor 100 or an object to which the sensor 100 is attached, from a certain height. In other embodiments, the threshold force may be determined using additional and/or other factors.

In some embodiments, the sensor 100 may also include a weight 109, which may be disposed at any point along the deformable beam 102, for example, proximal to the first end 104. The weight 109 may be, for example, metal, such as ball bearing, lead or steel shot, or any other material having a relatively high specific density compared to the material from which the deformable beam 102 is generally otherwise constructed. The weight 109 may be secured to the deformable beam 102 via any suitable process and/or device, such as adhesives, fasteners, wires, etc. The mass, size, placement, etc. of the weight 109 may serve additional design variables that may be adjusted so as to manipulate the threshold acceleration/impact forces that result in deformation of the deformable beam 102.

Figure 3:
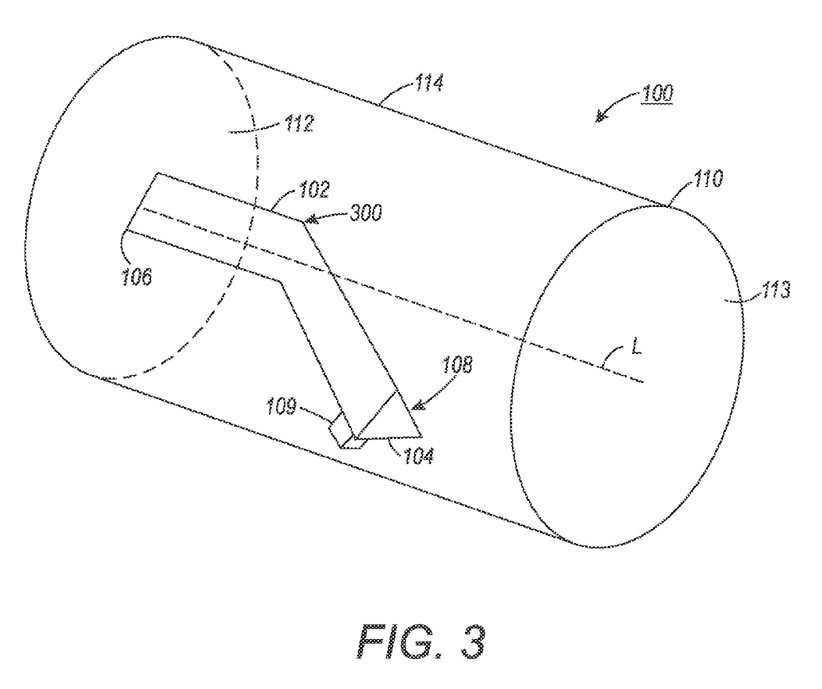
FIG. 3 illustrates another conceptual perspective view of the sensor, in a deformed position, according to an embodiment.

FIG. 3 illustrates the sensor 100 in a deformed configuration, defining a wrinkle 300 along the beam 102 between the first and second ends 104, 106. In various situations, the wrinkle 300 may be located in any position along the beam 102, closer to or proximal to either of the first and second ends 104, 106, and may not necessarily be in the middle of the beam 102. The wrinkle 300 may represent an area where the structural integrity of the deformable beam 102 has been compromised, for example, where the cross-section 108 has been at least partially crushed or otherwise deformed.

In operation, when the sensor 100 experiences a sufficient acceleration, e.g., caused by an impact of a package with which the sensor 100 is coupled falling onto the ground, a bending moment may be induced on the deformable beam 102. Such a bending moment may be enhanced by the presence of the weight 109, which may increase the inertia of the deformable beam 102 proximal to the first end 104. When the forces associated with the bending moment exceed the yield strength of the elongated beam 102, the deformable beam 102 may bend, resulting in the wrinkle 300.

Since the deformable beam 102 is generally not resilient, the wrinkle 300 may remain after the bending moment is no longer applied, i.e., after the shock/impact event. Accordingly, the deformable beam 102 including the wrinkle 300 may serve as an indicator that the sensor 100 and, by extension, the structure or package to which the sensor 100 is attached or otherwise associated, has received shock and/or impact forces indicative of mishandling.

The use of paper and/or polymer may also provide an anti-tamper feature for the sensor 100. If, for example, a user attempted to bend the deformed, deformable beam 102 back to its original configuration, the wrinkle 300 may remain visible. Accordingly, upon inspection, the history of impulsive forces (e.g., due to mishandling) may remain apparent, despite such attempted tampering.

Figure 4:
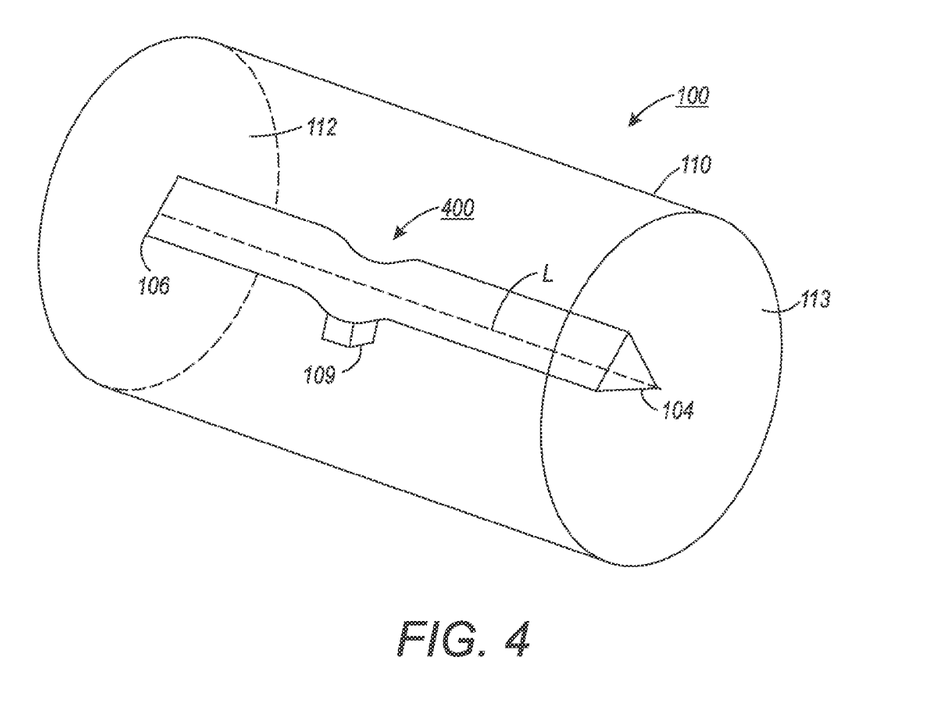
FIG. 4 illustrates a conceptual perspective view of the sensor in accordance with another embodiment.

FIG. 4 illustrates a perspective view of another embodiment of the sensor 100. In this embodiment, the deformable beam 102 is connected to the endwalls 112, 113 at both ends 104, 106, i.e., is simply supported by the housing 110. Accordingly, the weight 109 may be disposed between the ends 104, 106, for example, proximal the middle of the deformable beam 102. However, in some embodiments, the weight 109 may be omitted. Upon application of a sufficient acceleration (e.g., as indicative of a shock/impact event), the deformable beam 102 may deform (e.g., proximal the middle thereof), producing a wrinkle 400. This deformable beam 102 may have a deformed, e.g., at least partially crushed, cross-section 108 at the wrinkle 400. Accordingly, the deformable beam 102 may provide a visual indication of an impact force registered by the sensor 100.

Figure 5:
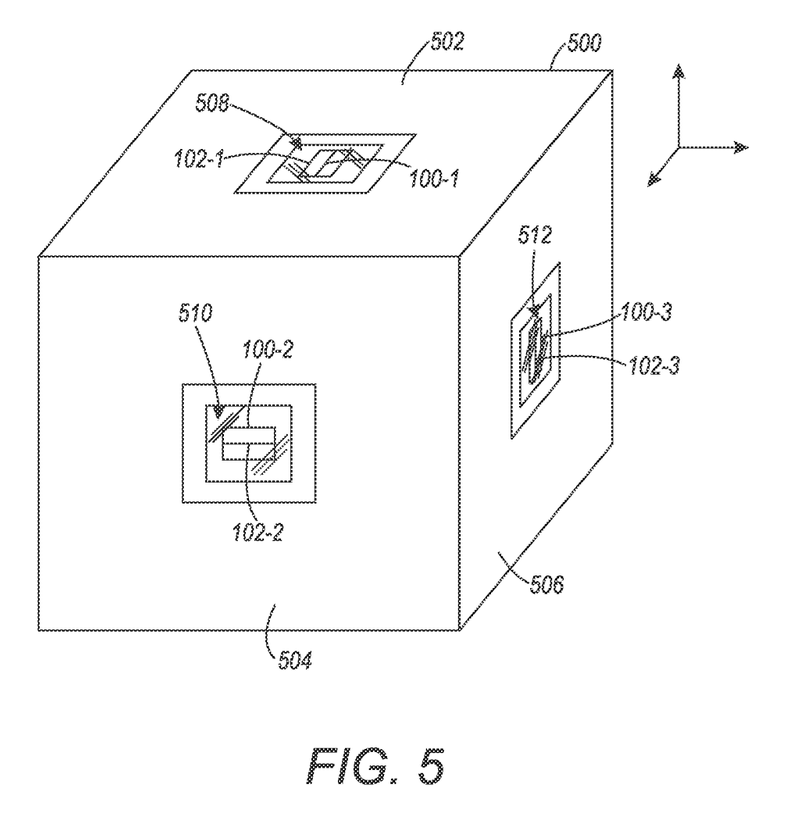
FIG. 5 illustrates a conceptual perspective view of a container employing three sensors, according to an embodiment.

FIG. 5 illustrates a perspective view of a package 500 in which three of the sensors 100 (specifically labeled as 100-1, 100-2, and 100-3) are employed, according to an embodiment. As shown, each of the sensors 100 may be disposed such that the beam 102-1, 102-2, 102-3 thereof is generally perpendicular to one of the axes (as shown), such that impact or shock forces along any, or a combination of, the axes may be detected by at least one of the sensors 100. The sensors 100-1, 100-2, 100-3 may each be disposed on a different face 502, 504, 506 of the package 500; however, in other embodiments, two or more, or even all, of the sensors 100-1, 100-2, 100-3 may be disposed on one of the faces 502, 504, 506. Accordingly, the illustrated configuration in which each sensor 100 is on a separate face is merely one example among many contemplated and should not be considered limiting.

In still other embodiments, the sensors 100-1, 100-2, 100-3 may be disposed within the package 500, for example, fixed to an interior side of a wall thereof, or disposed loose in the package 500. Furthermore, it will be appreciated that any number, e.g., one, two, three, four, five, or more sensors 100 may be employed for a given package 500, according to weight, sensitivity, shape of the package 500, or for any other reason. Moreover, in some instances, the sensor 100, or at least the deformable beam 102, may be visible through a transparent window 508, 510, 512 in the package 500.

Figure 6:
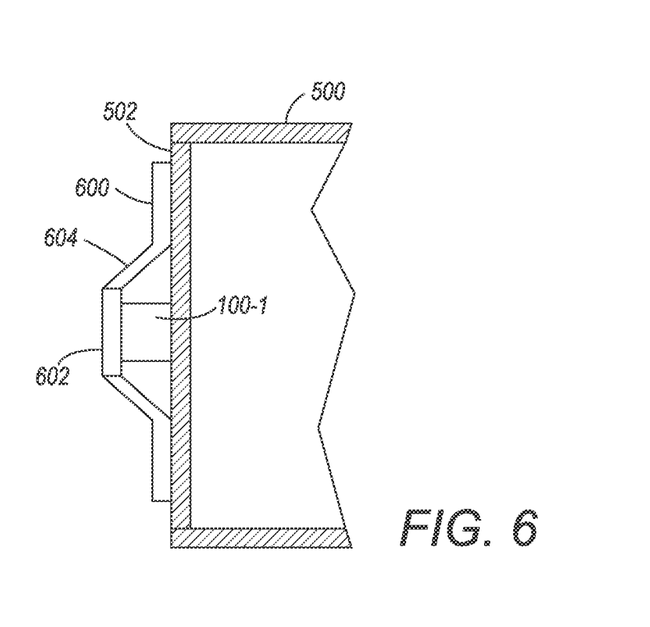
FIGS. 6 and 7 illustrate two partial, side cross-sectional views of the container, according to an embodiment.

FIG. 6 illustrates a side cross-sectional view of the sensor 100-1 fixed to the package 500, according to an embodiment. The sensor 100-1 may be secured to the exterior of the face 502, for example, using an adhesive label 600, which may be a flat and/or flexible sheet of any suitable material. In other embodiments, the sensor 100-1 may be secured directly to the package, for example, via an adhesive applied directly to the sensor 100-1, e.g., the housing 110 (FIG. 1).

In an embodiment, the label 600 may include a window 602. The window 602 may be made from a clear plastic, which may be secured to a border 604. In an embodiment, the border 604 may serve as a carrier for adhesive to secure the label 600 to the face 502; however, in other embodiments, the window 604 may additionally or instead carry the adhesive. In some cases, the border 604 may be opaque; however, in other embodiments, the border 604 may be translucent or transparent.

Figure 7:
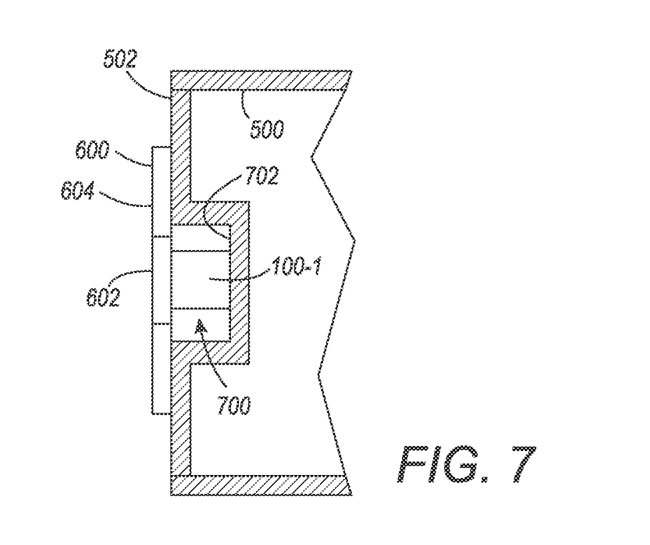

FIG. 7 illustrates a side cross-sectional view of the sensor 100-1 fixed to the package 500, according to another embodiment. As shown, the package 500 may define a cavity 700 extending inward from the face 502. The cavity 700 may be square, rounded, tubular, or any other shape. Further, the cavity 700 may be defined using flanges in the package 500 or formed into the package 500 using any suitable process or device such as, for example, by pressing a die into the face 502. The sensor 100-1 may then be positioned and may be secured (e.g., adhered) to a side 702 of the cavity 700, or may be left unsecured in the cavity 700. In some embodiments, the sensor 100-1 may not include the housing 110 (FIG. 1), and the deformable beam 102 may be secured directly to the package 500, e.g., to the side 702 of the cavity 700. The label 600 may then be fixed to the face 502, for example, so as to cover the cavity 700. The window 602 may be aligned with the cavity 700, e.g., the sensor 100-1, and may thus facilitate visual inspection of the sensor 100-1 from the exterior of the package 500.

Figure 8:
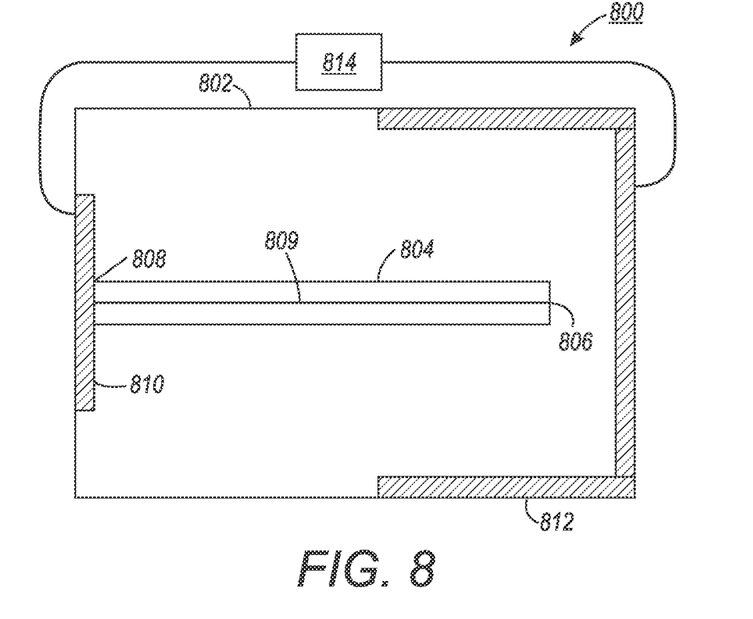
FIG. 8 illustrates a conceptual side view of another sensor, according to an embodiment.

FIG. 8 illustrates a schematic view of another sensor 800, according to an embodiment. As depicted, the sensor 800 may include a housing 802; however, like the sensor 100, the sensor 800 may, in some embodiments, omit the housing 802. Further, the sensor 800 may include a deformable beam 804, e.g., disposed in the housing 802. The deformable beam 804 may include a first end 806 and a second end 808. The deformable beam 804 may be coupled with the housing 802 proximal to the second end 808, for example, via adhesive, fasteners, etc. The first end 806 may be distal to the second end 808 and may not be connected with the housing 802, such that the deformable beam 804 may be disposed in a cantilevered configuration in the housing 802.

The deformable beam 804 may be formed from paper media, polymers, or combinations thereof, as described above, and may also include an electrically-conductive element 809. The conductive element 809 may be, for example, a metallic trace, coating, inlay, or the like, and may allow the deformable beam 804 to conduct electricity between the first and second ends 806, 808. In some embodiments, the conductive element 809 may include a contact pad, i.e., a relatively wide area of electrically conductivity, proximal to the first end 806. Further, the sensor 800 may include a first electrical contact 810 and a second electrical contact 812, which may be disposed on (e.g., coated, painted, metalized, adhered, or otherwise fixed to) the housing 802 or to any other structure, for example, when the housing 802 is omitted. The first and second electrical contacts 810, 812 may form part of a circuit that may be connected with a transmission device 814, such as an active or passive radio-frequency identification (RFID) tag.

The first and second electrical contacts 810, 812 may be separated, for example, disposed on opposite ends of the housing 802, as shown. In an embodiment, the first contact 810 may be disposed in contact with the second end 808 of the deformable beam 804, such that the first contact 810 may be electrically connected with the conductive element 809. The second contact 812 may be disposed separated from, but aligned with, the first end 806 of the deformable beam 804, when the deformable beam 804 is not, or not sufficiently, bent or otherwise deformed from its non-deformed configuration, as shown. The second contact 812 may, however, be disposed such that displacement of the first end 806 with respect to the housing 802, e.g., by bending the deformable beam 804, causes the first end 806 to contact the second contact 812 such that the conductive element 809 is electrically connected with the second contact 812. Further, the second contact 812 may be aligned with, e.g., surround the first end 806, as shown, such that displacement of the first end 806 in any direction may result in contact therewith.

In at least one embodiment, the deformable beam 804 may not be resilient, but may "permanently" deform, as explained above, for example. In another embodiment, however, the deformable beam 804 may be constructed from a resilient material, such as a metal, spring, wire, combinations thereof, etc. that may allow the first end 806 to deflect into engagement with the second contact 812 and then return to, or near to, its original configuration, separated from the second contact 812.

Figure 9:
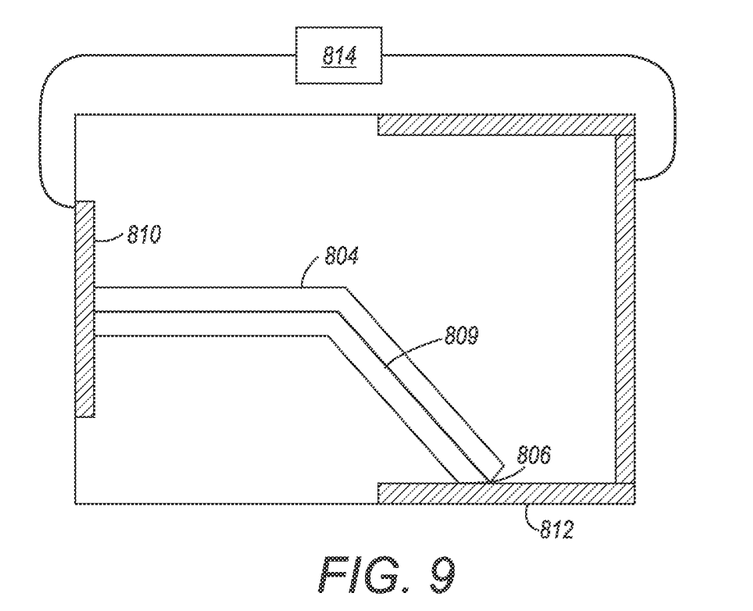
FIG. 9 illustrates a conceptual side view of the sensor of FIG. 8 in a deformed position, according to an embodiment.

FIG. 9 illustrates a schematic view of the sensor 800 when the beam 804 is deformed, according to an embodiment. As shown, when the deformable beam 804 is acted upon by a sufficient impact force, causing a bending moment in the cantilevered deformable beam 804, the first end 806 thereof may be displaced toward and into contact with the second contact 812. In this position, the conductive element 809 may electrically connect the first and second contacts 810, 812, thereby closing a circuit with the device 814.

At least when the circuit is closed, the transmission device 814 may transmit either continuously or in response to an excitation signal received from a reader. In another embodiment, when the switch is closed a certain number of times (e.g., once, twice, etc.), the transmission device 814 may be activated and continue to be activated, for example, despite the deformable beam 804 no longer connecting the first and second contacts 810, 812. In other embodiments, the transmission device 814 may be writable and may store an indication that the circuit was closed (and/or how many times it was closed) and may allow access to such data, e.g., via connection with a reading device. Further, in still other embodiments, other types of devices may be coupled with the sensor 800.

Accordingly, the impact registered by the sensor 800 may cause the device 814 to transmit or otherwise indicate that the impact has been received. Further, the circuit, once closed, may remain closed, as the deformable beam 804 may not be resilient and, once bent, may remain bent such that the first end 806 remains in contact with the second contact 812. In other embodiments, the deformable beam 804 may be resilient and may register multiple impact events and/or may deflect back to or near to its original position, opening the circuit between the first and second contacts 810, 812.

Figure 10:
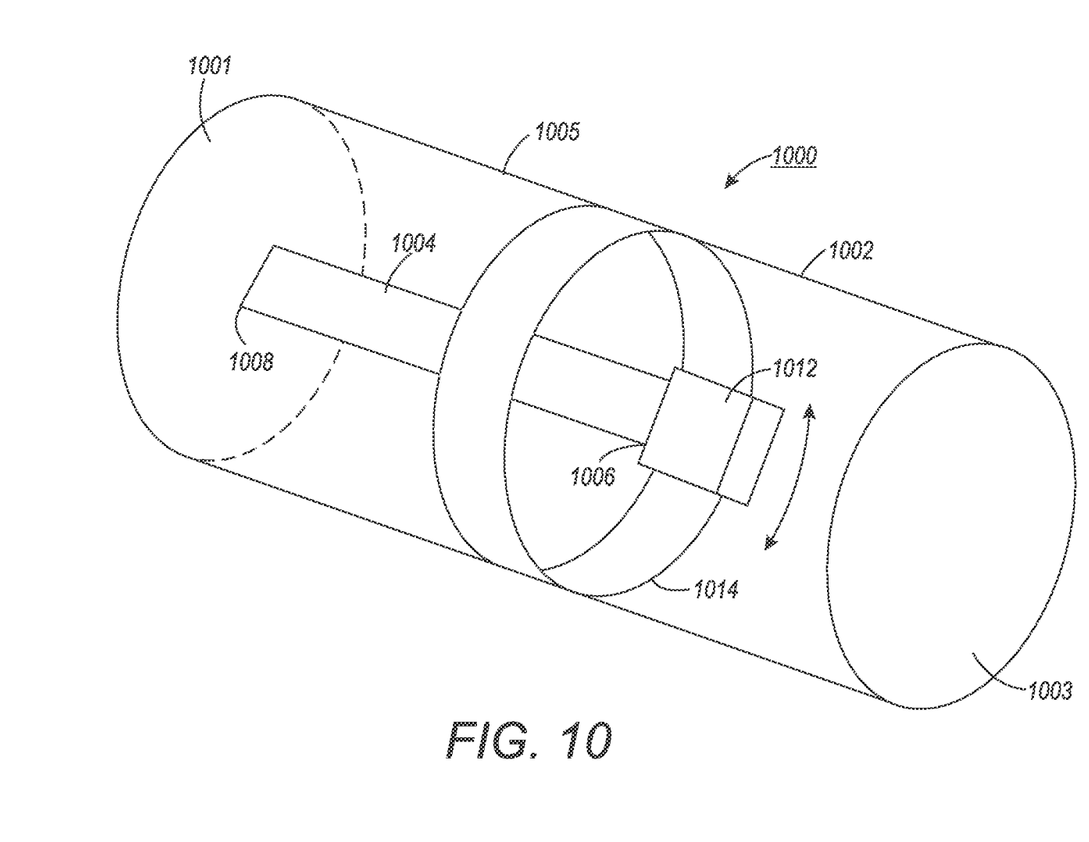
FIG. 10 illustrates a conceptual perspective view of yet another sensor, according to an embodiment.

FIG. 10 illustrates a side perspective view of another sensor 1000, according to an embodiment. The sensor 1000 may include a housing 1002; however, in other embodiments, the housing 1002 may be omitted. The sensor 1000 may also include a deformable beam 1004 having a first end 1006 and a second end 1008, with at least the second end 1008 being secured to the housing 1002. Further, in the illustrated embodiment, the housing 1002 includes endwalls 1001, 1003 and at least one sidewall 1005. The first end 1006 may be not be connected to the housing 1002, and thus the deformable beam 1004 may be disposed in a cantilevered configuration in the housing 1002. The deformable beam 1004 may have any suitable cross-section such as, for example, one or more of the cross-sections 108 discussed above. Further, the sensor 1000 may further include a head 1012 coupled to the first end 1006, which in some cases may be denser than the deformable beam 1004, so as to serve a function similar to the weight described above, or may have a generally similar density as the deformable beam 1004.

In another embodiment, the first and second ends 1006, 1008 of the deformable beam 1004 may be coupled with the endwalls 1001, 1003, respectively. In such an embodiment, the head 1012 may be coupled to the deformable beam 1004 between the first and second ends 1006, 1008. Moreover, with the ends 1006, 1008 secured to the endwalls 1001, 1003, the deformable beam 1004 may be constructed from a flexible material, such as a metal band, wire, spring, combinations thereof, etc., so as to allow the deformable beam 1004 to resiliently bend when a force is applied, and then return to, or near to, its original configuration. Similarly, in some of the cantilevered embodiments of the deformable beam 1004, the beam 1004 may be provided by such a flexible material, such that the beam 1004 may resiliently return to or near to its original configuration after deformation.

In at least one embodiment, the housing 1002 may have a chemical coating 1014 therein, and/or the head 1012 may also have a chemical coating. In other embodiments, one or both of the housing 1002 and the head 1012 may be at least partially constructed from a material configured to activate or be activated by a coating and/or the material of the other one of the housing 1002 and the head 1012. The coating(s) and/or materials may be configured such that activation thereof causes a visual indicator of the contact. In still other embodiments, the head 1012 and/or the housing 1002 may include a marking material, such as a paint or the like, which the other of the housing 1002 and the head 1012 may be configured to receive and show.

Accordingly, in operation of the sensor 1000, similar to the operation of the sensor 100, when an impact force is applied to the sensor 1000, a bending moment is applied through the deformable beam 1004. This may lead to the deformable beam 1004 bending, such that the head 1012 contacts the housing 1002, causing activation of the coating, exchange of the marking material and/or other chemicals, etc. As such, upon contact between the head 1012 and the housing 1002, a visual indicator, may be apparent on either the head 1012 and/or the housing 1002.

Further, as shown, in at least on embodiment, the housing 1002 may be tubular and the coating 1014 may be disposed in a stripe on the tubular sidewall 1005 at a generally constant axial location on the housing 1002. Accordingly, the sensor 1000 may be capable of illustrating impact, causing the head 1012 to contact the housing 1002, along two axes. Further, the sensor 1000 may be capable of showing multiple instances of reception of impact force, for example, as long as the impact force is along a different direction from previous impact forces, such that the head 1012 contacts the housing 1002 at different locations on the coating 1014.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

While the present teachings have been illustrated with respect to one or more implementations, alterations and/or modifications may be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. Furthermore, to the extent that the terms "including," "includes," "having," "has," "with," or variants thereof are used in either the detailed description and the claims, such terms are intended to be inclusive in a manner similar to the term "comprising." Further, in the discussion and claims herein, the term "about" indicates that the value listed may be somewhat altered, as long as the alteration does not result in nonconformance of the process or structure to the illustrated embodiment. Finally, "exemplary" indicates the description is used as an example, rather than implying that it is an ideal.

Other embodiments of the present teachings will be apparent to those skilled in the art from consideration of the specification and practice of the present teachings disclosed herein. It is intended that the specification and examples be considered as exemplary only, with a true scope and spirit of the present teachings being indicated by the following claims.

What is claimed is:
1. A sensor for detecting impact, comprising:
a deformable beam comprising a first end, a second end, and an elongated body extending therebetween, wherein:
at least the second end is coupled to a support structure;

the deformable beam is configured to bend from a first configuration to a deformed configuration when the sensor experiences an acceleration above a predetermined threshold; and the deformable beam is constructed at least partially from paper, such that a structural integrity of the deformable beam is compromised when the deformable beam deforms from the first configuration to the deformed configuration.

2. The sensor of claim 1, wherein the first end is not connected to the support structure, such that the deformable beam is cantilevered from the support structure.

3. The sensor of claim 1, wherein the first end of the deformable beam is coupled to the support structure, such that the deformable beam is simply supported by the support structure.

4. The sensor of claim 1, further comprising a housing at least partially surrounding the deformable beam, wherein the housing comprises the support structure.

5. The sensor of claim 1, further comprising a weight coupled with the deformable beam.

6. The sensor of claim 1, wherein the deformable beam defines a cross-section, the cross-section being selected from the group consisting of a circle, an ellipse, a torus, a polygon, an L-shape, and an I-shape, wherein the cross-section is at least partially crushed when the deformable beam deforms from the first configuration to the deformed configuration.

7. The sensor of claim 1, wherein the deformable beam comprises a combination of polymer and paper.

8. The sensor of claim 1, further comprising:
a housing comprising the support structure to which the deformable beam is coupled; and
a coating disposed on an inside of the housing, wherein the coating is configured to react to contact with the first end of the deformable beam, a head attached to the deformable beam, or both, so as to provide a visual indication of contact with the deformable beam.

9. The sensor of claim 1, wherein the deformable beam resiliently deflects from the first configuration to the deformed configuration and at least nearly back to the first configuration.

10. The sensor of claim 1, further comprising:
a first electrical contact coupled with the second end of the deformable beam; and
a second electrical contact separated from at least partially aligned with the first end of the deformable beam in the first configuration,
wherein at least a portion of the deformable beam is electrically conductive,
wherein, when the deformable beam is in the deformed configuration, the first end of the deformable beam contacts the second electrical contact, electrically connecting the first and second electrical contacts via the deformable beam, and
wherein the first end is spaced apart from the second electrical contact when the deformable beam is not in the deformed configuration.

11. The sensor of claim 10, wherein the first and second contacts are electrically coupled with a transmission device, such that electrically connecting the first and second contacts completes an electrical circuit that includes the transmission device.

12. A package, comprising:
a plurality of faces; and
a first sensor coupled with at least one of the plurality of faces, wherein:
the first sensor comprises a deformable beam comprising a first end, a second end, and an elongate body extending therebetween;
at least the second end is positionally fixed to a support structure;
the deformable beam is configured to deflect from a first configuration to a deformed configuration when the first sensor experiences an acceleration above a predetermined threshold; and
the deformable beam is constructed at least partially from paper, such that a structural integrity of the deformable beam is compromised when the deformable beam deforms from the first configuration to the deformed configuration.

13. The package of claim 12, further comprising a second sensor and a third sensor, wherein each of the first, second, and third sensors is configured to detect acceleration along a different axis.

14. The package of claim 12, wherein the first sensor further comprises a housing at least partially surrounding the deformable beam, wherein the housing provides the support structure to which the second end of the deformable beam is positionally fixed.

15. The package of claim 12, wherein the at least one of the plurality of faces provides the support structure to which the second end of the first sensor is positionally fixed.

16. The package of claim 12, wherein the deformable beam is supported from the support structure in a cantilevered configuration.

17. The package of claim 12, wherein the deformable beam is further constructed at least partially from a polymer.

18. The package of claim 12, wherein the deformable beam defines a wrinkle at least when the deformable beam is displaced.

19. An apparatus for detecting impact force on a container, comprising:
a housing comprising an endwall and a sidewall, wherein the endwall and the sidewall at least partially define an interior of the housing; and
a deformable beam comprising a paper, a polymer, a coated paper, or a combination thereof, wherein the deformable beam further comprises first and second ends, the second end being coupled with the endwall of the housing and the first end being distal to the second end and free to move in the interior of the housing, such that the deformable beam is supported from the endwall as a cantilever, or the first end is coupled with a second endwall of the housing such that the deformable beam is simply supported in the housing,
wherein at least a portion of the deformable beam defines a visible wrinkle when and after the apparatus experiences an acceleration above a predetermined threshold.

* * * * *